United States Patent [19]

Noguchi et al.

[11] Patent Number: 4,716,897
[45] Date of Patent: Jan. 5, 1988

[54] ELECTROSURGICAL APPARATUS

[75] Inventors: Toshiaki Noguchi, Tokyo; Seiichi Hosoda, Shirakawa; Ichiro Nakamura, Tokyo, all of Japan

[73] Assignee: Olympus Optical Co., Ltd., Tokyo, Japan

[21] Appl. No.: 881,646

[22] Filed: Jul. 3, 1986

[30] Foreign Application Priority Data

Jul. 15, 1985 [JP] Japan .................. 60-155527
Jul. 31, 1985 [JP] Japan .................. 60-168980

[51] Int. Cl.[4] ........................................... A61B 17/39
[52] U.S. Cl. ........................ 128/303.15; 128/303.17
[58] Field of Search ............... 128/303.13–303.18, 128/421–423, 419 D; 324/126

[56] References Cited

U.S. PATENT DOCUMENTS 2,771,554 11/1956 Gratze ........................... 128/421
3,747,605 7/1973 Cook ............................. 129/419 D
4,057,063 11/1977 Gieles et al. ................. 128/303.17

FOREIGN PATENT DOCUMENTS 2517955 6/1983 France ........................... 128/303.13
58-94845 6/1983 Japan .
1024776 4/1966 United Kingdom ............. 128/421

Primary Examiner—Lee S. Cohen
Attorney, Agent, or Firm—Frishauf, Holtz, Goodman & Woodward

[57] ABSTRACT

An electrosurgical apparatus includes a radio frequency (RF) power source for supplying an RF signal to an object to be cauterized through a treatment tool and an electrode plate. A dummy load with a certain impedance is coupled in the current path from an active terminal to which the treatment tool is connected to the check terminal connectable to an electrode plate. Before electrosurgical treatment, the dummy load is connected to the active terminal and the check terminal. An actual RF signal flowing through the dummy load is detected and compared with a predetermined RF signal from the RF power source.

4 Claims, 24 Drawing Figures

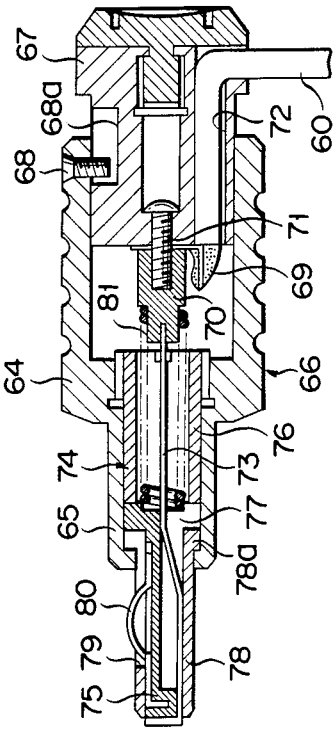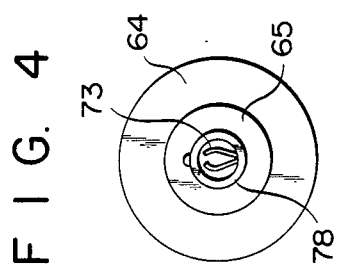

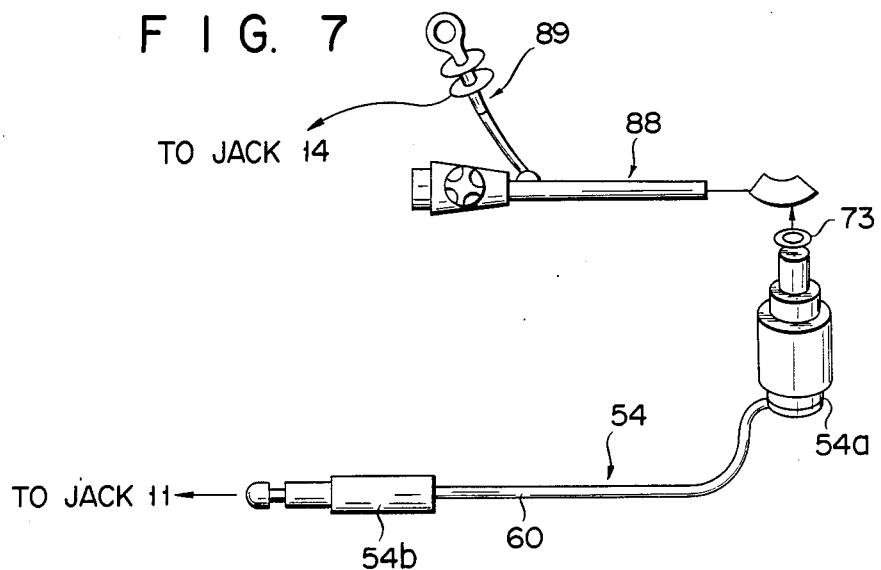
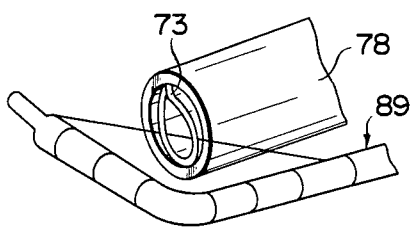
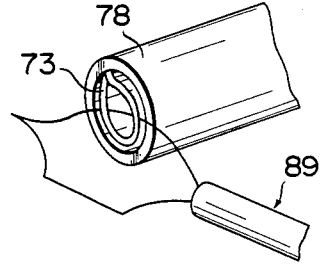
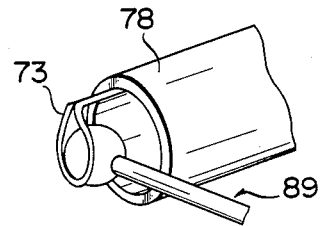
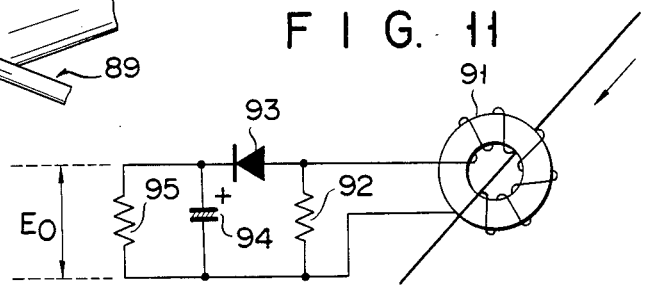

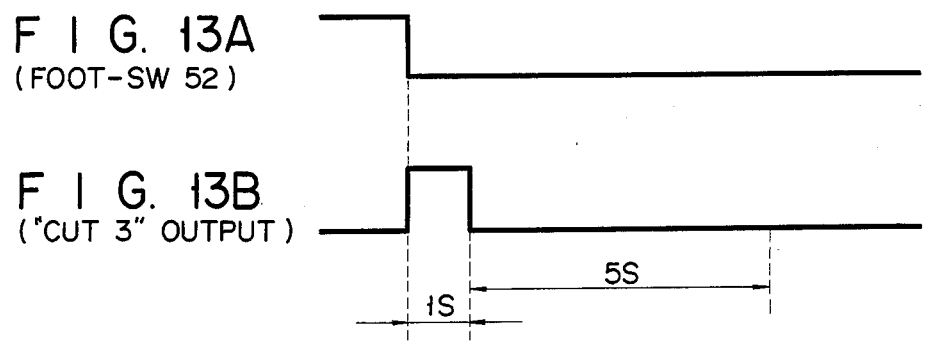
FIG. 13A
(FOOT-SW 52)
FIG. 13B
("CUT 3" OUTPUT)
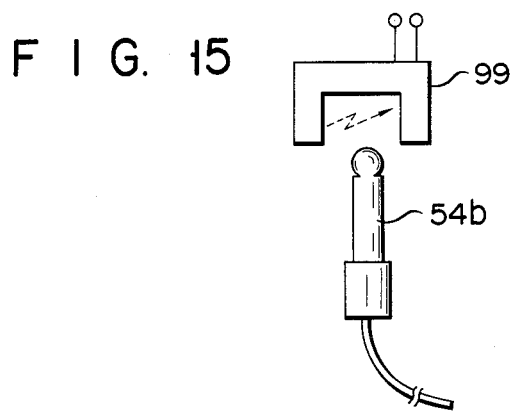
FIG. 15
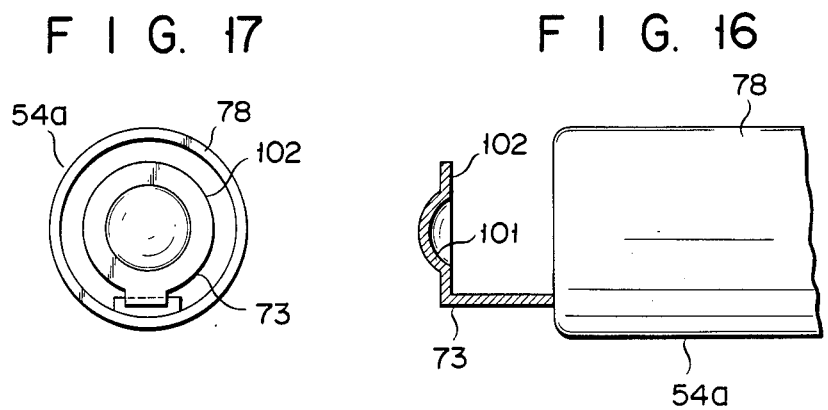
FIG. 17
FIG. 16

F I G. 18
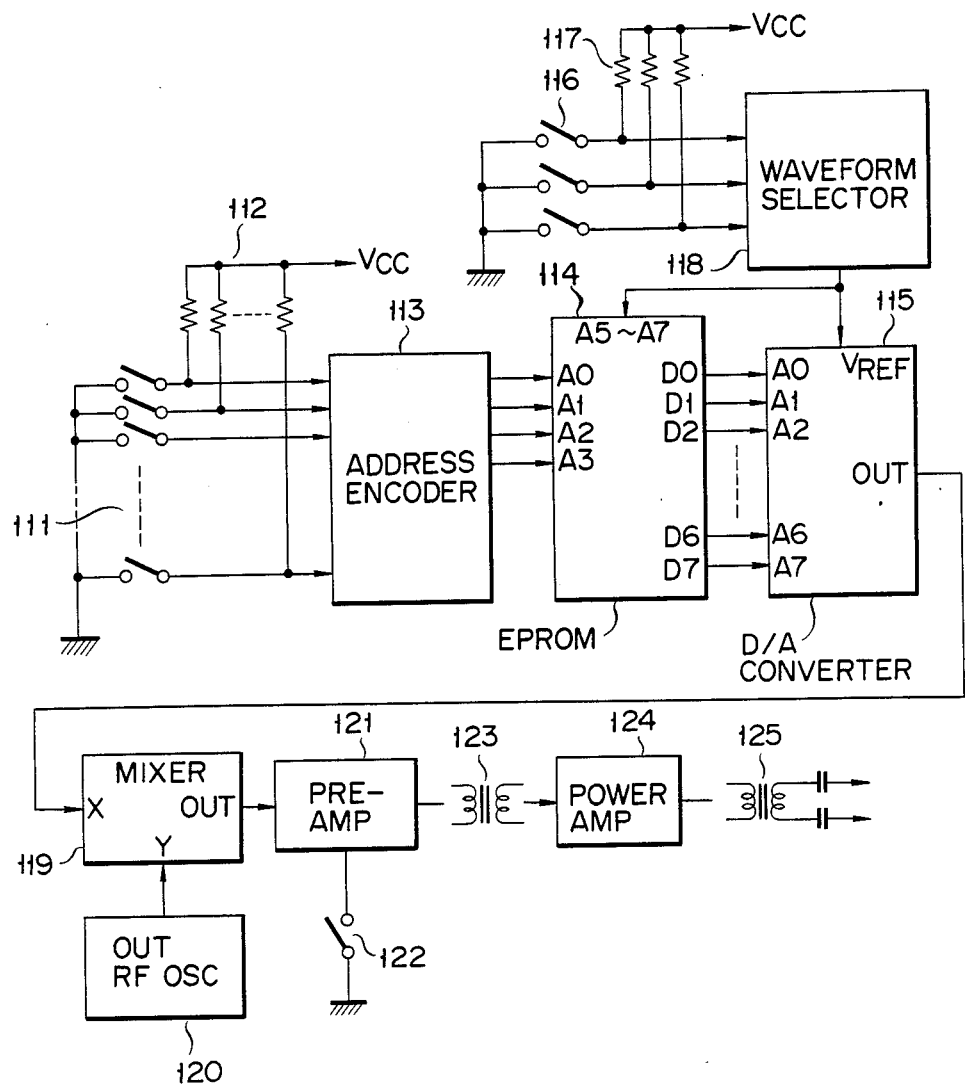

F I G. 21A
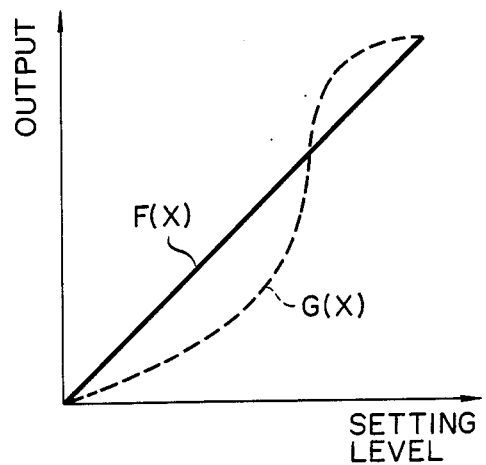
F I G. 21B
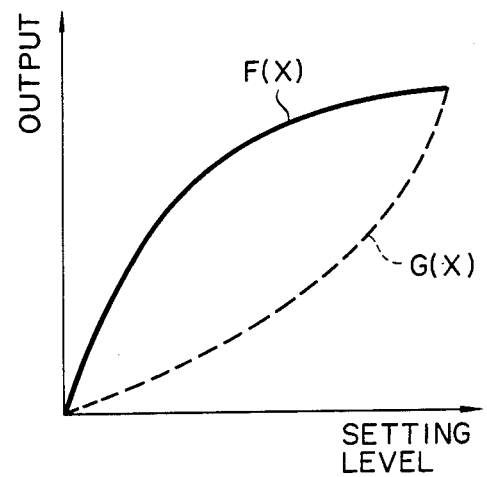

ELECTROSURGICAL APPARATUS

BACKGROUND OF THE INVENTION

The present invention relates to an electrosurgical apparatus and, more particularly, to an operation check therefor.

Electrosurgical apparatuses called "electric knives" have been in widespread use in a variety of medical and machine applications in recent years. An RF (radio frequency) current or high frequency current is supplied to an object to be cauterized or tooled and the object is seared or cut. The degree of cautery is determined by an RF current value flowing through the object, and the RF current can be controlled to a proper level by an output level setting switch or the like.

In setting an RF current value to a desired value, accurate correspondence between the value preset by the level setting switch and the actual output current value must be checked in advance. This check is particularly required in the field of medical treatment. For example, if the actual output current value is higher than the preset value, the large current endangers a patient. Therefore, before a surgical operation is performed, an operator or doctor must check in advance if output corresponding to the value preset by output setting switches is accurately produced.

A conventional electrosurgical apparatus mainly includes an RF power source, a treatment tool (an active electrode) such as a stainless wire connected to the RF power source, and an electrode plate (a passive electrode) connected to the RF power source and mounted on the patient's body. An RF current is supplied between the tip of the treatment tool and the electrode plate through the patient's body to burn or sear abnormal or injured tissue.

Japanese Patent Disclosure (Kokai) No. 58-94845 describes a conventional method of checking an RF output. According to this method, an incandescent lamp as a dummy load in place of the patient's body is connected between the tip of the treatment tool and the electrode plate. A value set by a level control switch is manually changed to visually check change in brightness level of the incandescent lamp, thus performing the preoperation check.

According to this conventional method, however, special wiring is required to connect the incandescent lamp between the electrode plate and the tip of the treatment tool, and its preparation is time-consuming and cumbersome. In addition, the brightness level of the incandescent lamp is visually checked, resulting in an inaccurate output level check. According to this conventional method, an overall system operation check including checking of a foot switch for designating an ON state of the RF current is impossible.

A clip is arranged at one end of an output check incandescent lamp cord to clamp the treatment tool, thereby providing an electrical connection therewith. However, since the tip of the treatment tool is clamped by the clip, it is often damaged by a sharp hook portion since the clip has a structure wherein a phosphor bronze plate having a width of about 2 mm is bent in a hook-like shape. If a hemostat having a rounded tip is used as the treatment tool, the clamp cannot firmly clasp the rounded tip. As a result, a proper electrical connection for the operation check cannot be achieved.

The output level can be set by changing the amplitude of the RF signal input to an amplifier for amplifying the RF output. In order to change the amplitude, a resistance ratio of an input resistance of the amplifier is changed by using a variable or fixed resistor switch.

In the conventional output level setting method, an actual output is often higher than the setting value due to variations in gain of the amplifier and poor linearity. The variations in gain of the amplifier can be controlled by a semi-fixed resistor. However, the resistance of the semi-fixed resistor varies according to vibrations, and a contact resistance varies in use over a long period of time. Even if the resistance is corrected, the preset value cannot be maintained for a long period of time. In addition, when linearity is poor, desired characteristics cannot be obtained regardless of the amplifier gain. In this case, the output setting resistance ratio must be changed. However, the resistance as a function of the rotational angle cannot be changed in a potentiometer. Alternatively, if fixed resistors are used, resistors having different resistances are changed over by using a switch.

If the output level setting value is commonly used for different output waveforms, for cutting, coagulating, and blend, a single resistance ratio is used to produce three different outputs. In this case, different variation and linearity characteristics are obtained in the different output waveforms. If three output waveforms, for cutting, coagulating, and blend, are to be selectively and independently obtained, different output level setting means can be arranged for the respective output waveforms. However, the circuit arrangement is undesirably complicated in addition to requiring cumbersome adjustment.

SUMMARY OF THE INVENTION

It is an object of the present invention to provide a simple and safe electrosurgical apparatus capable of accurately checking if an RF current output value accurately corresponds to a preset value.

It is another object of the present invention to easily set desired output characteristics in response to output setting values of the electrosurgical apparatus, and to easily update the preset value.

In order to achieve the above objects of the present invention, there is provided an electrosurgical apparatus comprising a dummy load arranged in a housing, an RF (radio frequency) output source for outputting a predetermined RF signal, a connection line for connecting the dummy load and the RF output source, a detector for detecting an actual RF signal flowing through the dummy load, and a comparator for comparing the predetermined RF signal from the RF output source with the actual RF signal detected by the detector.

BRIEF DESCRIPTION OF THE DRAWINGS

FIG. 3 is a longitudinal sectional view of a first plug of an output check connection cord used in the first embodiment;

FIG. 4 is a cross-sectional view of the first plug of the output check connection cord used in the first embodiment;

FIG. 5 is a longitudinal sectional view showing a state wherein the first plug of the connection cord is inserted in an active jack;

FIG. 6 is a longitudinal sectional view showing a state wherein the second plug of the connection cord is inserted in a check jack;

FIG. 7 is a perspective view showing a connection state for checking an RF output from an endoscopic treatment tool;

FIG. 8 is a perspective view showing a connection state for checking an output through a papillotomy knife as an endoscopic treatment tool;

FIG. 9 is a perspective view showing a connection state for checking an output through an RF snare as an endoscopic treatment tool;

FIG. 10 is a perspective view showing a connection state for checking an output through a hemostat as an endoscopic treatment tool;

FIG. 11 is a circuit diagram of a current detector in the output check circuit in FIG. 2;

FIGS. 13A and 13B are timing charts for explaining the operation of the first embodiment;

FIG. 15 is a schematic diagram showing a modification of a check-mode detector used in the first embodiment;

FIG. 16 is a longitudinal view showing a modification of the first plug of the connection cord;

FIG. 17 is a cross-sectional view showing a modification of the first plug of the connection cord;

FIG. 18 is a circuit diagram of an electrosurgical apparatus according to a third embodiment of the present invention;

FIGS. 21A and 21B are respectively graphs showing RF output level characteristics so as to explain the operation of the third embodiment.

DETAILED DESCRIPTION OF THE PREFERRED EMBODIMENTS

Figure 1:
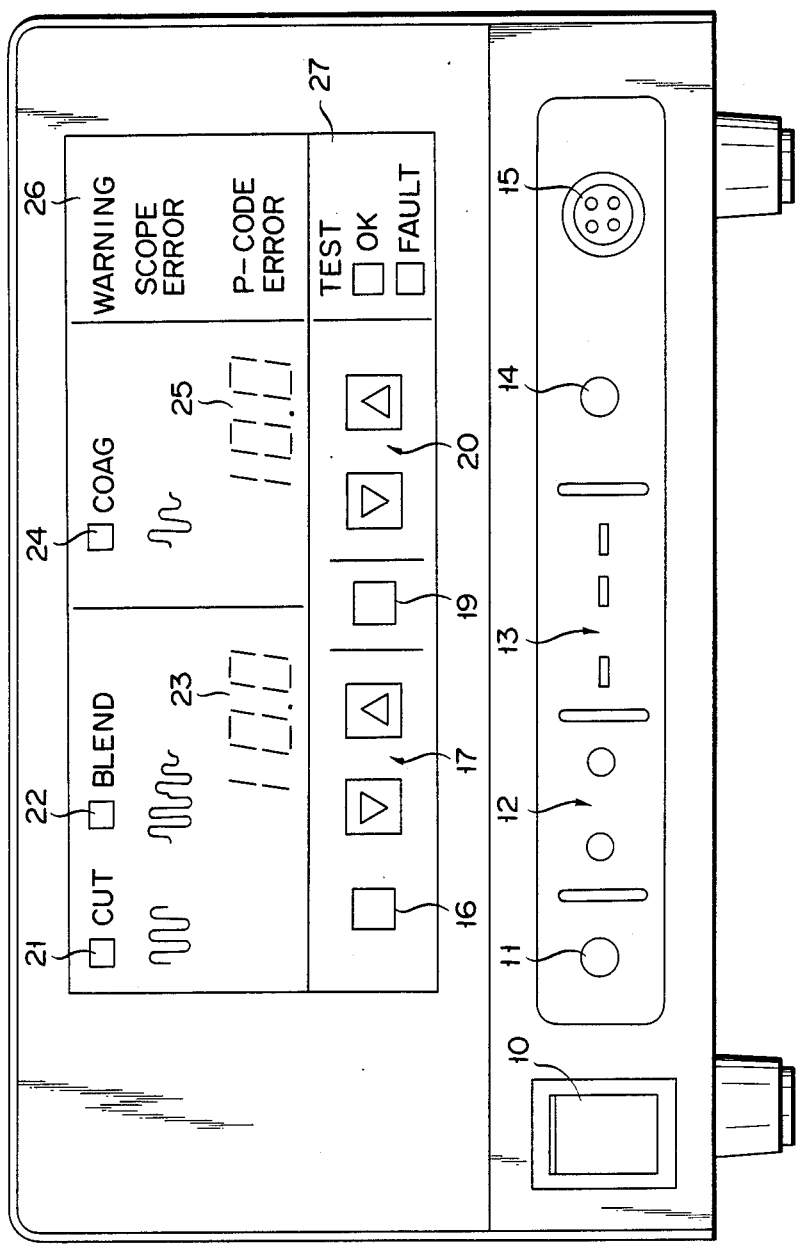
FIG. 1 is a plan view showing an operation panel of an electrosurgical apparatus according to a first embodiment of the present invention.
Figure 2:
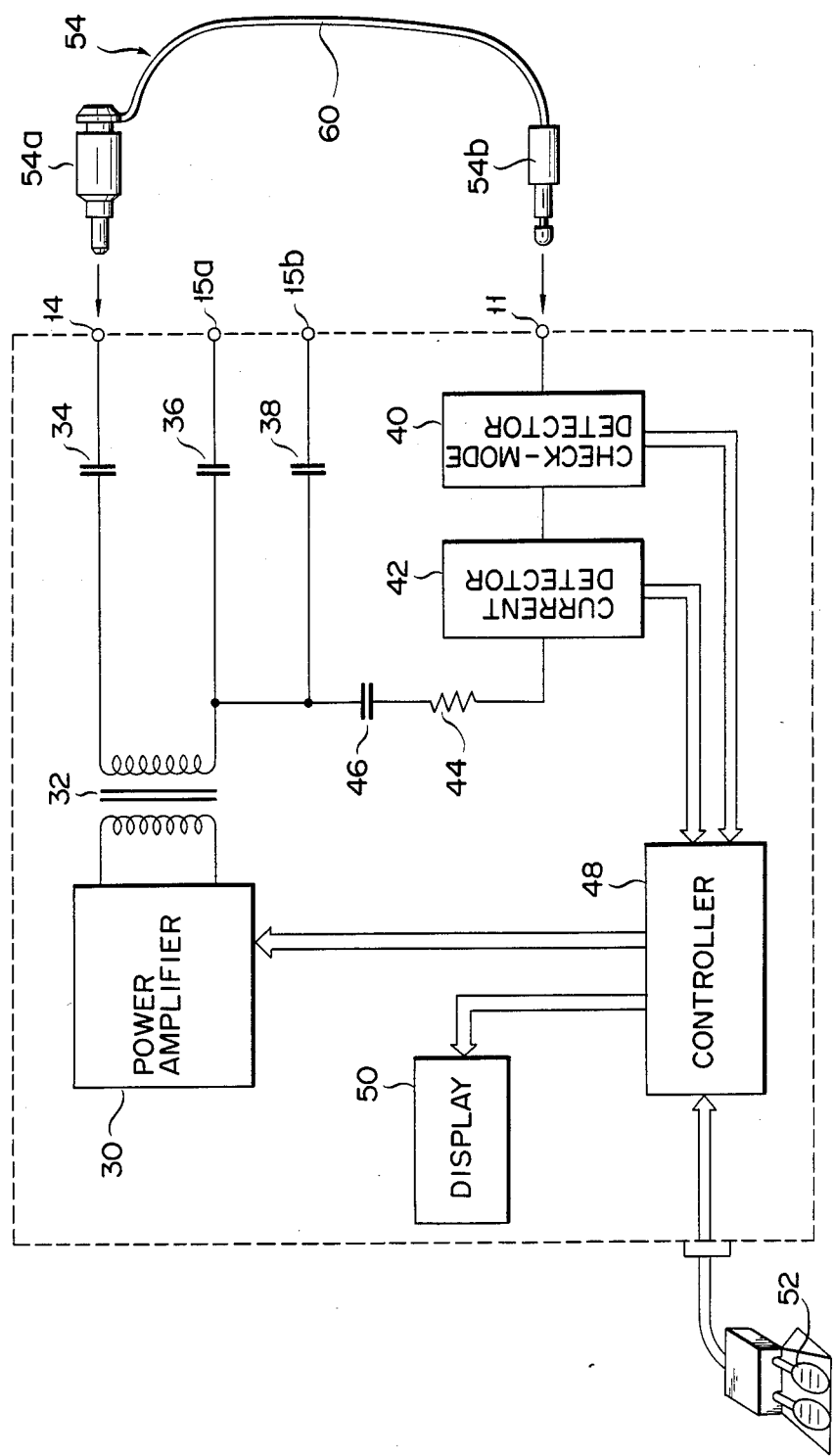
FIG. 2 is a circuit diagram of an output check circuit of the first embodiment.

Electrosurgical apparatuses according to preferred embodiments of the present invention will be described with reference to the accompanying drawings. FIG. 1 is a front view of an operation panel supported by a housing of an electrosurgical apparatus according to a first embodiment of the present invention, and FIG. 2 is a circuit diagram of the first embodiment. Power switch 10 is arranged at the lower left corner of the operation panel shown in FIG. 1. Jacks are arranged to the right of switch 10. These jacks are check jack 11 connected to second plug 54b of connection cord 54 (FIG. 2) during an output check, jack 12 connected to a bipolar electrode plug, jack 13 connected to a plug of a knife holder with a hand switch, active jack 14 which is connected to an active cord connected to a treatment tool during cauterization and is connected to first plug 54a of connection cord 54 during the output check, and patient jack 15 connected to a 4-pin S-P or P cord (i.e., a patient electrode).

Operation switches and display elements are arranged in the upper half of the operation panel. The operation switches are mode selection switch 16 for selecting a cutting or blend mode, output control switches 17 for controlling a cutting or blend output, coagulating switch 19 for selecting a coagulating mode, and output control switches 20 for controlling a coagulating output. The display elements are mode indicator lamps 21, 22, and 24 for indicating the cutting, blend, and coagulating modes, digital display 23 for displaying a numeric value in the cutting or blend mode, digital display 25 for displaying a setting value in the coagulating mode, warning monitor 26 for displaying a check result, and output check indicators 27.

FIG. 2 is a circuit diagram of the first embodiment. This diagram only illustrates an RF current output check function associated with the invention of the present application, and other arrangements are omitted. Only check terminal 11, active terminal 14, and patient terminals 15a and 15b to be connected to the P cord are illustrated as terminals representing the jacks. In the output check mode, connection cord 54 is connected to check and active terminals 11 and 14. The output check circuit includes power amplifier 30 as an RF current source. The output current is supplied to active terminal 14, patient terminals 15a and 15b, and check terminal 11 through RF transformer 32. An output current value of power amplifier 30 can be controlled by controller 48. Capacitors 34, 36, and 38 are respectively connected between transformer 32 and terminal 14, between transformer 32 and terminal 15a, and between transformer 32 and terminal 15b. Check terminal 11 is connected to RF transformer 32 through check-mode detector 40, current detector 42, dummy load 44, and capacitor 46.

Dummy load 44 is the same as the load of a path of a current flowing from active terminal 14 to patient terminals 15a and 15b through the treatment tool, the patient's body, and the patient electrode plate. In other words, the same current as the actual current flowing through the patient's body in response to a preset value from power amplifier 30 flows through dummy load 44.

Signals from check-mode detector 40 and current detector 42 are supplied to controller 48. Controller 48 controls power amplifier 30 and display 50, including the various display elements on the operation panel in FIG. 1. A signal from a foot switch 52 is supplied to controller 48 to provide output start timing of the RF current.

First plug 54a has structure shown in FIGS. 3 and 4. Plug 54a comprises a cylinder 66 with large-diameter and small-diameter portions 64 and 65. Slider 67 is slidably inserted in large-diameter portion 64 of cylinder 66. Guide groove 68a is formed in the outer surface of slider 67. Guide pin 68 extending on the wall surface of large-diameter portion 64 is engaged with guide groove 68a. Therefore, the sliding range of slider 67 is defined by guide pin 68 and does not fall off large-diameter portion 64. Piece 70 is fixed by screw 71 to the inner end face of slider 67 through conductive plate 69 by way of solder. Through hole 72 is formed in slider 67 to receive one end of cable 60 connecting the first and second plugs. Cable 60 is connected to conductive plate 69. One end of clamper 73 made of a wire is mounted to the end face of piece 70. Clamper 73 is inserted in hollow shaft 74 meshed with the inner surface of small-diameter portion 65. Small-diameter distal end portion 75 of hollow shaft 74 extends from small-diameter portion 65 of cylinder 66. Notch 77 is formed in distal end portion 75 to communicate with an inner space of proximal end portion 76 of hollow shaft 74. Clamper 73 is inserted in notch 77. The other end of clamper 73 is looped and opposes the distal end face of distal end portion 75 of hollow shaft 74. Outer tube 78 is fitted on distal end portion 75 and is fixed to cylinder 66 through collar 78a formed at one end portion of tube 78. Slit 79 is axially formed in the outer surface of outer tube 78. An arcuated portion of leaf spring 80 held on the outer surface of distal end portion 75 of hollow shaft 74 extends from slit 79. Coil spring 81 is hooked between piece 70 and the inner end face of proximal end portion 76 of hollow shaft 74. Spring 81 biases slider 67 so that it is removed from large-diameter portion 64 of cylinder 66. Clamper 73 is electrically connected to cable 60 of connection cord 54 through piece 70 and leaf spring 80. If slider 67 is slid against the biasing force of spring 81, clamper 73 is moved together with slider 67 so that its bent distal end opposes the distal end surface of hollow shaft 74. Leaf spring 80 extending from outer tube 78 is brought into elastic contact with output jack 14 when first plug 54a is inserted in output jack 14, as shown in FIG. 5.

Second plug 54b comprises proximal portion 82, conductive portion 83 extending from proximal portion 82, and insulating portion 84 formed at the distal end portion of conductive portion 83, as shown in FIG. 6. If second plug 54b is inserted in output check jack 11, conductive portion 83 is brought into contact with electric contact 85 and insulating portion 84 is brought into contact with lever 86 of check-mode detector 40, thereby operating detector 40.

As shown in FIG. 7, in order to check if a normal output is produced from treatment tool 89 connected to active jack 14 and inserted in endoscope 88, second plug 54b of cord 54 is connected to output check jack 11, and first plug 54a is connected to the distal end portion of tool 89 extending from endoscope 88. More specifically, slider 67 of first plug 54a is pushed and the distal end portion of tool 89 is elastically clamped between the distal end portion of clamper 73 and the distal end face of hollow shaft 74 by the return force of spring 81. If tool 89 is a papillotomy knife (FIG. 8) or an RF snare (FIG. 9), its wire is clamped. However, if tool 89 is a hemostat, as shown in FIG. 10, its spherical distal end is clamped. Since the distal end portion of tool 89 is elastically clamped by clamper 73 obtained by bending a wire in an arcuated shape, the distal end portion of tool 89 is not damaged by clamper 73. In addition, even if the distal end of tool 89 has a shape (e.g., a spherical shape) which does not allow easy clamping, it can be properly clamped.

FIG. 11 shows a detailed arrangement of current detector 42. Controller 48 detects a current flowing through dummy load 44 and determines whether a predetermined RF current corresponding to the preset value flows. A current flowing through dummy load 44 is detected by a current sensor comprising coil 91, resistor 92, diode 93, capacitor 94, and resistor 95. The normal/error value of the RF output can then be detected according to voltage $E_0$ applied to resistor 95.

Figure 12:
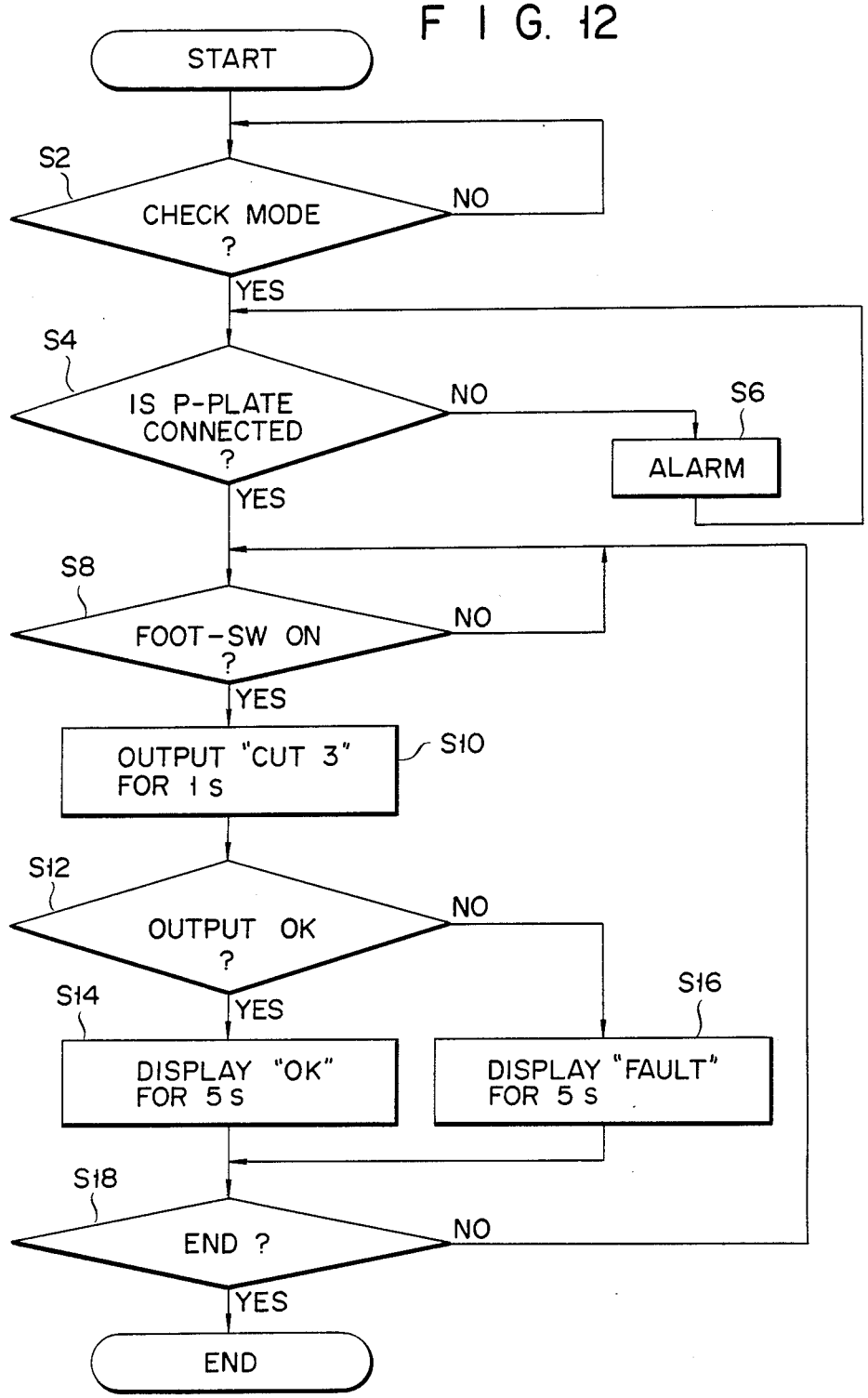
FIG. 12 is a flow chart for explaining the operation of the first embodiment.

The operation of the first embodiment will be described with reference to the flow chart in FIG. 12. When operation is started, controller 48 determines in step S2 whether the check mode is selected, i.e., whether connection cord 54 is inserted in check jack 11 for performing an output check. Step 2 is repeated until insertion of connection cord 54 is detected. If YES in step 2, controller 48 checks in step S4 whether the plug of the patient electrode (P plate) is connected to patient jacks 15a and 15b. This decision block is executed since the contents of the output check include P cord connection. If NO in step S4, an alarm is generated in step S6. Step S4 is repeated until the connection is detected.

If YES in step S4, controller 48 determines in step S8 whether foot switch 52 is turned on. Step S8 is repeated until foot switch 52 is turned on. Upon detection of the ON state of switch 52, power amplifier 30 is controlled in step S10. An RF current of "CUT3" is output for one second. One-second output is meant to stabilize the output to some extent while preventing heating of the dummy load. The output of "CUT3" is one of various possible setting outputs in the electrosurgical apparatus. The output levels include "CUT1" (minimum level) to "CUT10" (maximum level) in unitary increments, i.e., a total of ten levels. An RF current output from power amplifier 30 is supplied from one end of RF transformer 32 through capacitor 34, connection cord 54, check-mode detector 40, current detector 42, dummy load 44, and capacitor 46 to the other end of RF transformer 32.

Controller 48 determines in step S12 whether the current corresponding to "CUT3", based on the detected value of detector 42 for detecting the current flowing through load 44, flows through load 44. If YES in step S12, "OK" output check indicator 27 on the operation panel is turned on for 5 seconds in step S14. However, if NO in step S12 (either an excessively high or low current is detected), "FAULT" output check indicator 27 is turned on for 5 seconds in step S16.

This state is indicated in FIGS. 13A and 13B. More specifically, when foot switch 52 is turned on to set an output signal at low level, as shown in FIG. 13A, "CUT3" is output for one second and the following 5-second period is the output check result indication period, as shown in FIG. 13B. Therefore, the operator is informed whether the RF output corresponding to the preset value is produced. During the 5-second period, the RF output is not generated to prevent the dummy load from overloading, even if the foot switch is depressed.

Controller 48 determines in step S18 whether the check operation is completed. If NO in step S18, the flow returns to step S8. Otherwise, the routine is ended.

According to the first embodiment as described above, dummy load 44 having the same load as that during cauterization is arranged in the housing. Check jack 11 and active jack 14 are connected through connection cord 54 so that dummy load 44 is connected to power amplifier 30 as an RF current source. Thus, the same current as in cauterization can flow through the dummy load 44 and therefore RF output check can be easily performed with accuracy. The check operation is started only when the patient electrode is connected. The output is produced in response to a signal from foot switch 52. The preset value check, as well as the patient electrode connection state check and the connection state check for foot switch 52 can be performed. As a result, an overall system check can be achieved.

Figure 14:
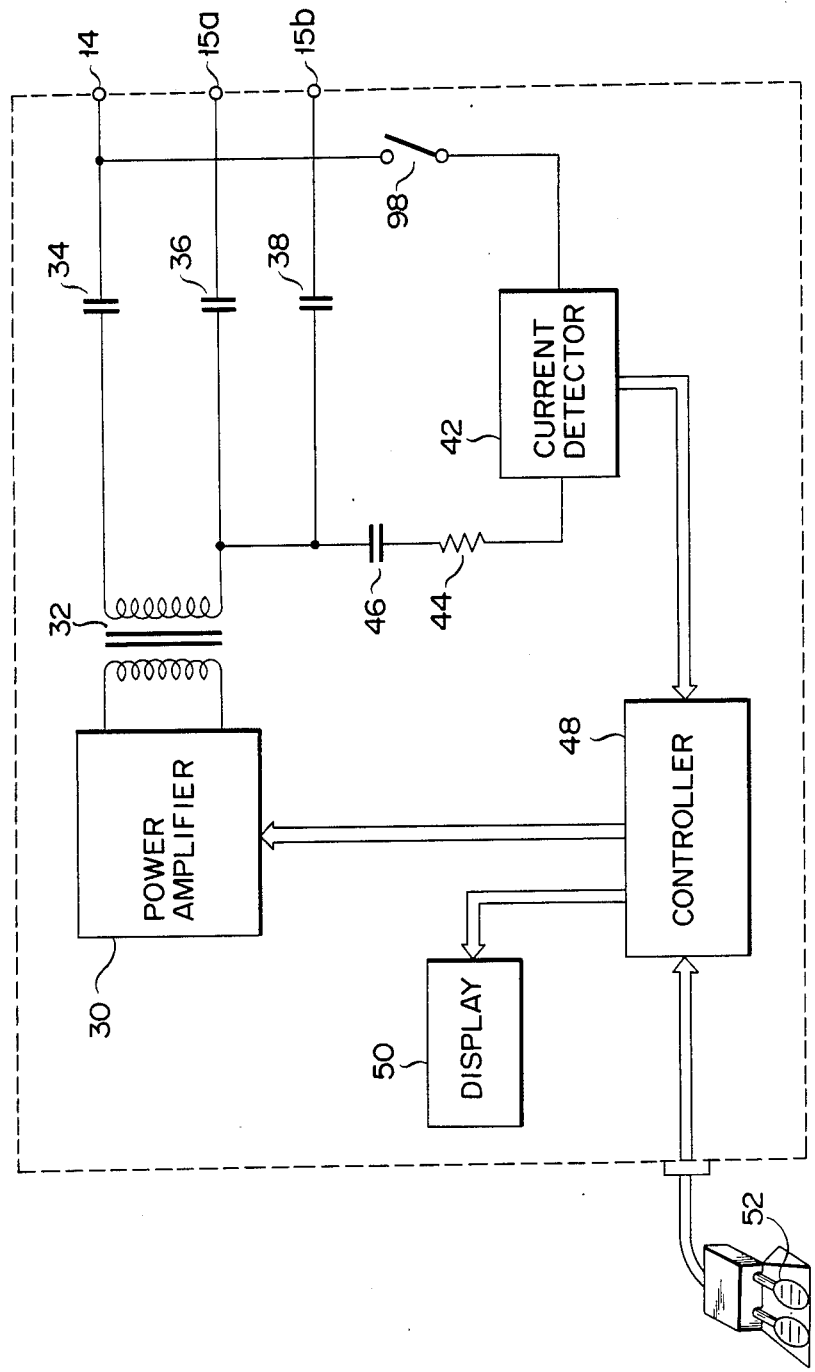
FIG. 14 is a circuit diagram of an output check circuit in an electrosurgical apparatus according to a second embodiment of the present invention.

In the first embodiment, check jack 11 is connected to active jack 14 through connection cord 54, and thus dummy load 44 is connected to power amplifier 30. However, the connection mode is not limited to the one described above. As shown in FIG. 14, switch 98 can be connected between current detector 42 and active jack 14, and current detector 42 can be electrically connected to or disconnected from active jack 14 upon on/off operation of switch 98 according to a second embodiment.

The present invention is not limited to the particular embodiments described above. Various changes and modifications may be made within the spirit and scope of the invention. In these embodiments, the output check is performed for specific preset value "CUT3". However, the preset value can be sequentially changed to check all corresponding outputs. The electrosurgical apparatus is not limited to medical applications but can be extended to industrial applications as well.

FIG. 15 shows a modification of check-mode detector 40. Insertion of second plug 54b of connection cord 54 into check jack 11 is detected and hence designation of the output check mode is detected. If the distal end of plug 54b crosses the optical path of photocoupler 99, designation of the output check mode can be detected. Similar P cord insertion detectors (not shown) are connected to patient jacks 15a and 15b.

FIGS. 16 and 17 correspond to FIGS. 3 and 4, and show a modification of first plug 54a. Clamper 73 is not made of a wire but of a metal band. The distal end of clamper 73 comprises clamping piece 102 with a flat circular shape, and recess 101 of an arcuate cross section. With this structure, the distal end portion of treatment tool 89 will not be damaged, as it is not in the above embodiments. In addition, even if the distal end portion of tool 89 is spherical, it can be properly held.

A third embodiment of the present invention will be described. The third embodiment is associated with setting of output values of RF currents CUT1 to CUT10, etc.

In the embodiment of FIG. 18, output level setting switch 111 is constituted by 10 switch elements respectively corresponding to output levels CUT1 to CUT10. The switch elements are connected to power source Vcc through resistors in resistor circuit 112 and to input terminals of address encoder 113. The address output terminals of encoder 113 are connected to address signal input terminals A0 to A3 of EPROM (Erasable Programmable Read-Only Memory) 114. EPROM 114 stores a data table including data corresponding to the various output levels. In this case, cutting, coagulating, and blend data tables may be stored in EPROM 114. Output level data is read out in response to an address signal from address encoder 113. Data terminals D0 to D7 of EPROM 114 are respectively connected to input terminals A0 to A7 of D/A converter 115.

Output waveform selection switches 116 are connected to resistor circuit 117 and waveform selector 118. Selection switches 116 are cutting, coagulating, and blend output waveform switches. These switches are respectively connected to the resistors in resistor circuit 117. The output terminal of waveform selector 118 is connected to reference voltage terminal VREF of D/A converter 115. Output terminal OUT of D/A converter 115 is connected to input terminal X of mixer 119. Input terminal Y of mixer 119 is connected to output terminal OUT of RF oscillator 120. Output terminal OUT of mixer 119 is connected to the input terminal of preamplifier 121. Foot switch 122 is connected to preamplifier 121. The output terminal of preamplifier 121 is connected to the primary winding of drive transformer 123. The secondary winding of drive transformer 123 is connected to the input terminal of power amplifier 124. The output terminal of power amplifier 124 is connected to the primary winding of output transformer 125. The secondary winding of output transformer 125 is connected to a treatment tool (the patient electrode and the RF knife or snare) through terminals 14, 15a, 15b, and 11 in FIG. 2.

The operation of the third embodiment will be described below. An output waveform is selected by one of switches 116. Waveform selector 118 generates an output corresponding to a selected waveform, e.g., a cutting waveform. Output setting switches 111 are selectively operated to set a desired output level. Address encoder 113 converts the output level to corresponding address data, which accesses a specific address of EPROM 114. Output level data is then read out from a memory area at the accessed address of EPROM 114. When output level data is input to D/A converter 115, it supplies a cutting waveform signal representing a cutting waveform with a set output level to mixer 119. Mixer 119 mixes the cutting waveform signal with an RF signal, i.e., modulates the RF signal with the cutting waveform signal. The modulated signal is then input to preamplifier 121. In this case, if foot switch 122 is closed, the modulated signal is amplified by preamplifier 121, and the amplified signal is supplied to drive transformer 123. A secondary winding output from transformer 123 is supplied to output transformer 125 through power amplifier 124. Thereafter, a cutting current is output from the output transformer 125.

Since the RF output level is controlled on the basis of level data stored in the EPROM, the preset value does not vary and can be easily updated by modifying the data table.

Figure 19:
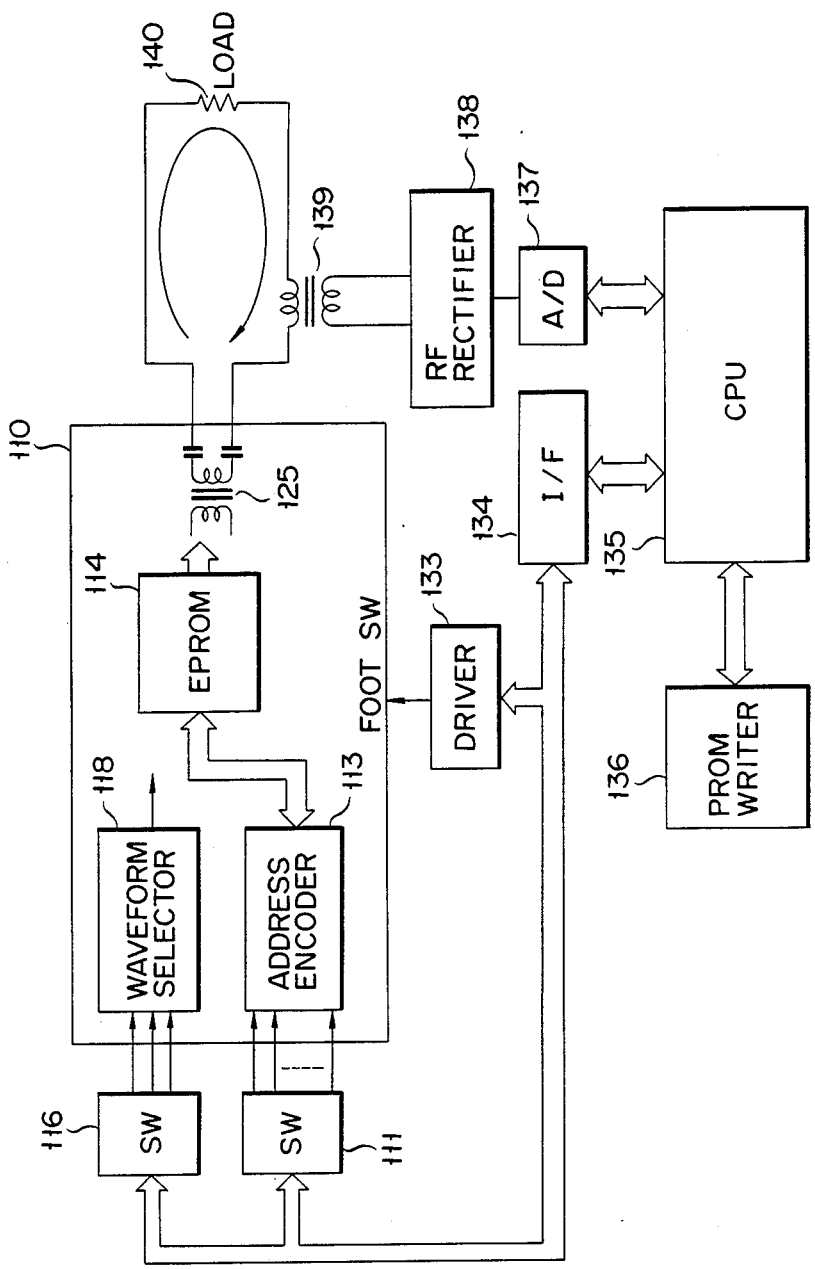
FIG. 19 is a circuit diagram of a system for automatically measuring the output characteristics of the third embodiment and producing an output level table.

FIG. 19 shows a circuit for producing the data table written in EPROM 114. Block 110 in FIG. 19 corresponds to the circuit of FIG. 18. Switches 116 and 111 are connected to waveform selector 118 and address encoder 113. Switch driver 133 is arranged to operate foot switch 122. Switches 111 and 116, and switch driver 133 are connected to CPU 135 through interface circuit (I/F) 134. CPU 135 is connected to PROM writer 136 and to RF rectifier 138 through A/D converter 137. The input terminal of rectifier 138 is connected to load 140 through RF transformer 139.

The data table forming operation of the circuit in FIG. 19 will be described with reference to the flow charts of 20A and 20B. Measured data is prestored in EPROM 114 in circuit 110, and the operation is then started. The output waveform, i.e., one of the cutting, coagulating and blend waveforms is set by the corresponding one of switches 116. For example, the cutting waveform is selected (step S22). Waveform selector 118 outputs the cutting waveform signal.

Output level setting switches 111 are selectively used to set an output level (step S24). First, the minimum level "CUT1" is set. In this state, when switch driver 133 causes foot switch 122 to turn on (step S26), a cutting current of the minimum level is output from output transformer 125. This cutting current is supplied to load 40 through current detection transformer 139 so that it detects the load current. The RF cutting current detected by transformer 139 is rectified by RF rectifier 138. The rectified signal is supplied to A/D converter 137. Output data from A/D converter 137 is converted to data table data by CPU 135, and the converted data is stored in a memory in CPU 135 (step S28). In this case, the address space allocation is determined according to I (output waveform) = 1 to 3 and J (output level) = 1 to 10. The level data obtained upon the detection is stored at the corresponding address. Upon storage of the first data in the memory, output designation for the next output level is requested. In this case, when J=2, corresponding level data is read out from EPROM 114, and an RF cutting current with an output level corresponding to J=2 is output from output transformer 125. This current is detected by RF transformer 139. The detected current is supplied to CPU 135 through RF rectifier 138 and A/D converter 137 and stored as output level data at the corresponding address of the memory incorporated in the CPU. The above operation is repeated up to J=10 (step S30). The current detection data of J=1 to 10 is stored in the memory incorporated in the CPU, thereby creating the data table for cutting waveforms.

If cutting waveform data input is completed up to J=10, setting of another output waveform is requested (step S32). In this case, when the coagulating waveform, i.e., I=2 is set, the output level is sequentially input from J=1, and the coagulating waveform data table can be created in the same manner as for the cutting waveform data table. When the coagulating waveform data table is completely created, the blend waveform (I=3) is designated to create a corresponding data table as described above.

Figure 20A:
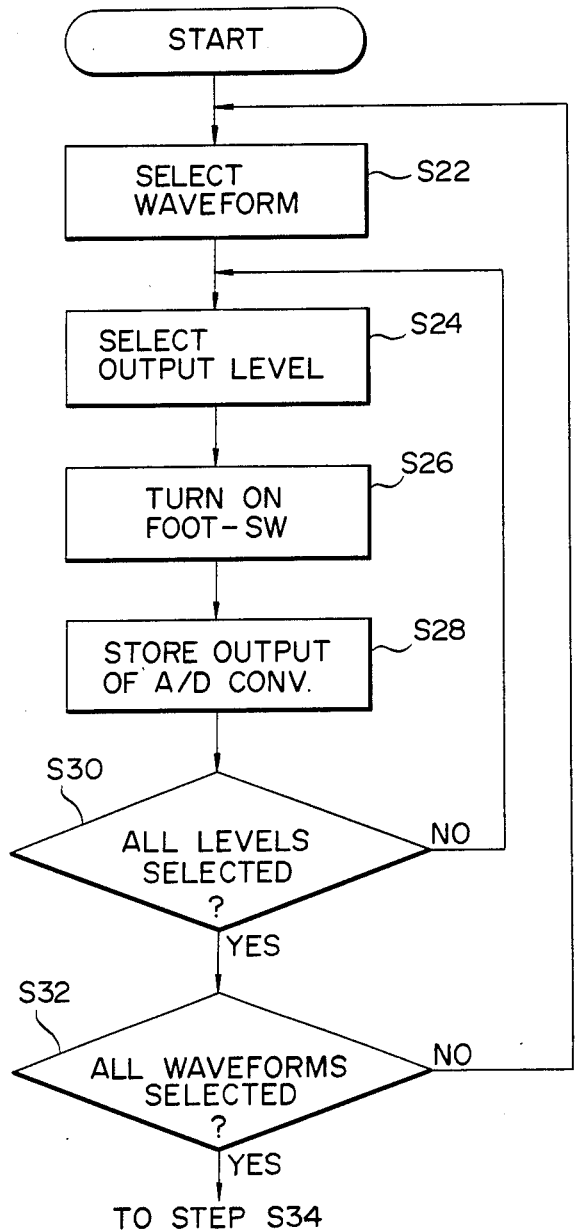
FIGS. 20A and 20B are respectively flow charts for explaining the operation of the third embodiment.
Figure 20B:
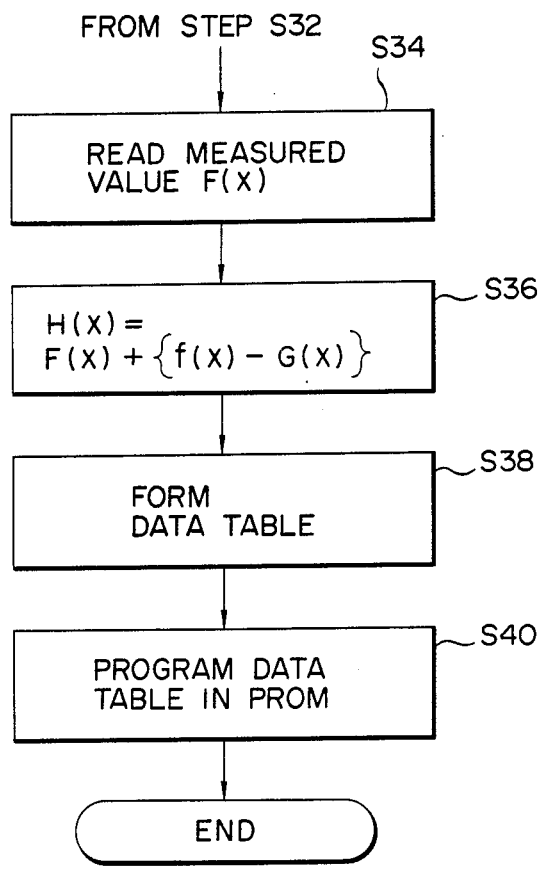

When processing for waveforms I=1 to 3 and output levels J=1 to 10 is completed, data table correction is performed. More specifically, data stored in the EPROM 114 is corrected according to the actually measured data. As shown in the flow chart of FIG. 20B, measured data is read out from the memory incorporated in the CPU (step S34). The measured data is represented by G(x), as shown in FIGS. 21A and 21B. Setting data in EPROM 114 is represented by F(x). It should be noted that the characteristics in FIGS. 21A and 21B vary according to the different waveforms.

Correction processing using measured and setting data are performed as follows (step S36):

$$H(x) = F(x) + \{F(x) - G(x)\}$$

In the above equation, x is changed from 1 to 10. The resulting corrected values are used to create a data table (step S38). The data obtained by the above calculation creates a curve symmetrical about measured data curve G(x) with respect to setting curve F(x). If the data obtained by the above calculation is used as the setting value, it is corrected in consideration of variations in gain of the output amplifier and poor linearity. If the output level of the electrosurgical apparatus is set according to the setting value, the output accurately corresponding to the setting value can be obtained.

The data table created by the data obtained by the above calculation is transferred to a PROM writer 136 and stored therein. In order to store the data table in PROM writer 136, data storage is performed such that a memory area at addresses excluding the necessary addresses is set as a zero output area. With this arrangement, output is zero even if addressing is wrong, thereby preventing the patient from being endangered.

The data table stored in PROM writer 136 is transferred to EPROM 114. The data table corresponding to the measured characteristics (characteristics of the output amplifier and the like) of the electrosurgical apparatus is stored (step S40). Therefore, an output accurately corresponding to the setting value can be produced by the electrosurgical apparatus.

In the above description, the respective output levels are minutely determined by calculations. However, several data tables may be prepared for similar characteristics and may be used according to the characteristics of the electrosurgical apparatus. Only one data table is required for an apparatus with small variations in the gain of the amplifier and good linearity. In addition, check data or the like may be stored in PROM writer 136.

In the above embodiment, the output level data is stored. However, this embodiment can be applied to a division ratio of the output waveform. For example, the embodiment can be easily applied to setting of a blend ratio, and setting of an interval between the burst waves of the coagulating waveform. It should be noted that the blend ratio is a ratio for blending the coagulating and cutting waveforms according to time division.

According to this embodiment, various RF output level data signals determined by the electrosurgical apparatus characteristics such as output amplifier characteristics are stored in a memory such as a PROM. The desired output level can be set by addressing of the memory so that the actual RF output accurately coincides with the setting value. Therefore, an RF output of an unexpected level is not produced and safe therapeutic treatment can be performed. The output level can be easily updated by modifying the contents of the memory. In addition, once the output level is set in the memory, the setting value will not vary according to deterioration over time or noise. Therefore, a cumbersome check operation required for the conventional electrosurgical apparatus can be omitted.

What is claimed is:

1. An electrosurgical apparatus, comprising:
    a housing;
    a dummy load arranged in said housing of said electrosurgical apparatus;
    radio frequency (RF) output means for outputting a predetermined RF signal;
    terminal means on said housing for enabling a connection between said dummy load and said RF output means, including a first terminal connected to said dummy load and a second terminal connected to said RF output means;
    means for detecting an actual RF signal flowing through said dummy load; and
    means for comparing a predetermined RF signal from said RF output means with an actual RF signal detected by said detecting means when said dummy load is connected to said RF output means, and for producing a fault alarm signal when the actual detected RF signal deviates excessively from said predetermined RF signal;
    wherein said connecting means comprises a connection cord arranged outside said housing for connecting said first terminal connected to said dummy load to said second terminal connected to said RF output means.

2. An electrosurgical apparatus according to claim 1, including an electrosurgical treatment tool for use with an endoscope, the tool having a distal end, and wherein said connection cord includes a plug detachably connectable to the distal end of said electrosurgical treatment tool, said plug being provided with a clamper extending from a distal end of said plug and adapted to elastically clamp said distal end of said treatment tool against the distal end of said plug.

3. An electrosurgical apparatus according to claim 1, in which said RF output means comprises:
    memory means for storing data of the predetermined RF signal when said detecting means detects a desired actual RF signal;
    output value setting means for setting the predetermined RF signal and reading out data corresponding to the predetermined RF signal from said memory means; and means for generating the desired actual RF signal in response to the data read out from said memory means by said output value setting means.

4. An electrosurgical apparatus according to claim 3, in which said memory means comprises an erasable programmable read-only memory for storing amplitude data corresponding to the predetermined RF signal.

* * * * *